United States Patent [19]

Onder et al.

[11] 4,156,065

[45] May 22, 1979

[54] CATALYTIC CONDENSATION OF ISOCYANATES AND CARBOXYLIC ACIDS OR ANHYDRIDES

[75] Inventors: Kemal B. Onder, North Haven; Curtis P. Smith, Cheshire, both of Conn.

[73] Assignee: The Upjohn Company, Kalamazoo, Mich.

[21] Appl. No.: 761,614

[22] Filed: Jan. 21, 1977

[51] Int. Cl.² .................... C08G 18/16; C08G 73/10
[52] U.S. Cl. ................. 528/51; 260/326 R; 260/558 R; 528/73; 528/84
[58] Field of Search ............ 260/47 CB, 775 R, 63 N, 260/326 R, 558 R; 528/51, 73, 84

[56] References Cited

U.S. PATENT DOCUMENTS

| | | | |
|---|---|---|---|
| 3,541,038 | 11/1970 | Nakano et al. | 260/30.6 |
| 3,697,484 | 10/1972 | Zecher et al. | 260/77.5 R |
| 3,708,458 | 1/1973 | Alberino et al. | 260/65 |
| 3,755,242 | 8/1973 | Reich | 260/37 N |

*Primary Examiner*—Lester L. Lee
*Attorney, Agent, or Firm*—Denis A. Firth; John Kekich

[57] ABSTRACT

An improved process is described for the reaction of an isocyanate (mono or poly) with a carboxylic acid or anhydride (mono or poly) to form the corresponding imide, amide or amide-imides. The improvement lies in using as the catalyst the 1-oxide, 1-sulfide or 1-hydrocarbylimino derivative of a phospholene, phospholane or phosphetane. The latter compounds are also substituted in the 1-position by a hydrocarbyl ($C_{1-12}$) or halohydrocarbyl ($C_{1-12}$) and may additionally carry one or more halo, lower-alkoxy, phenoxy, lower-hydrocarbyl or halo-substituted hydrocarbyl groups on the ring carbon atoms.

14 Claims, No Drawings

CATALYTIC CONDENSATION OF ISOCYANATES AND CARBOXYLIC ACIDS OR ANHYDRIDES

BACKGROUND OF THE INVENTION

1. Field of the Invention

This invention relates to the condensation of isocyanates with carboxylic acids or anhydrides to form imides, amides, or amide-imides and is more particularly concerned with the use of cyclic phosphorus compounds as catalysts for the condensation.

2. Description of the Prior Art

The reaction of isocyanates with carboxylic acids or anhydrides to form imides and amides, and, more particularly, the reaction of organic diisocyanates with dicarboxylic acids or dianhydrides, or anhydrides containing free carboxyl groups, to form polyamides, polyimides or polyamide-imides, is well-known; see, for example, U.S. Pat. Nos. 3,592,789; 3,541,038; and 3,708,458. The use of catalysts to promote these condensations is also known; see, for example, U.S. Pat. No. 3,701,756.

We have now found that the above reactions can be catalyzed in highly satisfactory manner using a group of heterocyclic phosphorus compounds which have not hitherto been suggested for this purpose. Our findings are particularly surprising in view of the known behaviour of this class of phosphorus compounds as catalysts for the conversion of isocyanates to carbodiimides. We have found that the compounds in question can be used to catalyze the above reactions of isocyanates with carboxylic acids and derivatives thereof without any significant concurrent formation of carbodiimides except in certain instances.

SUMMARY OF THE INVENTION

This invention comprises an improved process for catalyzing the reaction between an organic isocyanate and a member selected from the class consisting of organic carboxylic acids and organic carboxylic anhydrides wherein the improvement comprises employing as the catalyst a cyclic phosphorus compound selected from those having the formulae:

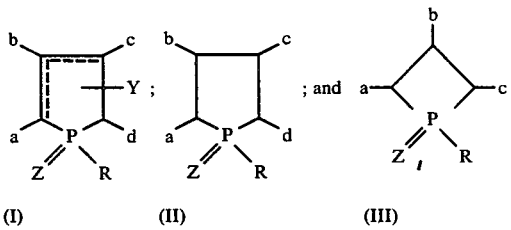

wherein a, b, c, and d in each instance are independently selected from the group consisting of hydrogen, halogen, lower-alkoxy, phenoxy, lower-hydrocarbyl, and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of lower-hydrocarbyl and halo-substituted lower-hydrocarbyl, and Z is selected from the class consisting of oxygen, sulfur, and NR', wherein R' is lower-hydrocarbyl.

The term "halogen" is used throughout this specification and claims in its generally accepted sense as embracing chlorine, bromine, iodine, and fluorine.

The term "lower-alkoxy" as used throughout the specification and claims means alkoxy from 1 to 6 carbon atoms, inclusive, such as methoxy, ethoxy, propoxy, butoxy, pentyloxy, hexyloxy and isomeric forms thereof. The term "lower-hydrocarbyl" means the monovalent radical obtained by removing one hydrogen atom from a parent hydrocarbon having from 1 to 6 carbon atoms, inclusive. Illustrative of such hydrocarbyl groups are alkyl such as methyl, ethyl, propyl, butyl, pentyl, hexyl and isomeric forms thereof; alkenyl such as vinyl, allyl, butenyl, pentenyl, hexenyl, and isomeric forms thereof; cycloalkyl such as cyclobutyl, cyclopentyl and cyclohexyl; and phenyl.

The term "halo-substituted lower-hydrocarbyl" means lower-hydrocarbyl as above defined wherein one or more of the hydrogen atoms in said hydrocarbyl has been replaced by halogen. Illustrative of halo-substituted lower-hydrocarbyl are chloromethyl, trichloromethyl, trifluoromethyl, 2-chloroethyl, 2,3-dichlorobutyl, 2-chlorobutenyl, 2-bromohexyl, 4-chlorophenyl, 3-fluorophenyl, 2-chloropropenyl, and the like.

DETAILED DESCRIPTION OF THE INVENTION

The essentially novel feature of the present invention resides largely in the employment of a heterocyclic phosphorus compound of the formulae (I), (II) or (III) as catalyst in the known reaction of an isocyanate with a carboxylic acid or anhydride to form the corresponding amide, imide or amide-imide. The procedure employed in carrying out the process of the invention is essentially that employed hitherto in this particular condensation with the exception that the heterocyclic phosphorus compound is present in the reaction mixture in catalytic amount corresponding to about 0.0001 mole to about 0.1 mole per mole of isocyanate. Preferably the amount of heterocyclic phosphorus catalyst employed is of the order of about 0.005 mole to about 0.05 mole per mole of isocyanate.

The process of the invention is applicable to the reaction of a monoisocyanate with a mono-carboxylic acid or a dicarboxylic acid anhydride to form a monomeric amide or imide, as well as to the reaction of a di- or polyisocyanate with a polyfunctional carboxylic acid or polyanhydride thereof as well as monomers containing both carboxylic anhydride and free carboxylic acid groups to form polyamides, polyimides and polyamide-imides.

The process of the invention is accomplished conveniently by bringing together the necessary reactants and the catalyst under substantially anhydrous conditions, advantageously, but not necessarily, in the presence of an inert organic solvent. By "inert organic solvent" is meant an organic solvent which is inert under the conditions of the reaction, i.e. does not enter into reaction with either of the reactants or the catalyst present in the reaction nor interfere with the desired progress of the reaction in any significant manner. Examples of such inert organic solvents are benzene, toluene, xylene, decalin, tetralin, chlorobenzene, dichlorobenzene, hexane, heptane, octane, dodecane, tetrahydrofuran, pyridine, dioxane, dimethylsulfoxide, dimethylformamide, N,N-dimethylacetamide, tetramethylene sulfone, dimethylsulfone, tetramethylurea, hexamethylphosphoramide, and the like.

The temperature employed in the reaction mixture can vary over a wide range from about 20° C. to about 250° C. but the reaction temperature is advantageously within the range of about 100° C. to 200° C. The most appropriate temperature to employ for any given combination of reactants can be readily determined by a process of trial and error.

The progress of the reaction is generally followed readily by standard analytical techniques, for example, by observing the appearance of absorption bands highly characteristic of the imide or amide linkages, as the case may be, using infrared spectroscopic analysis. When the reaction is observed to be complete, the desired product can be isolated from the reaction mixture by routine procedures, for example, by evaporation of the inert organic solvent, if one is used, followed by purification of the residue, if desired or necessary. Illustratively, when the product is monomeric, it can be purified by distilling out the heterocyclic phosphoric catalyst and subjecting the residue to recrystallization, distillation, and the like. When the product is a polymer, it can be purified after removing the catalyst as above, by trituration with inert organic solvent to remove low molecular weight by-products, or, where the polymer is soluble in an organic solvent, by precipitation from solution.

The isocyanate and the carboxylic acid or anhydride which are employed in the process of the invention are generally employed in substantially stoichiometric proportions.

The isocyanates which can be employed in the process of the invention include any of the known mono- and polyisocyanates such as those disclosed by Siefken, Ann. 562, 122–135 (1949). Illustrative of the isocyanates which are employed in the process of the invention are organic monoisocyanates such as phenyl isocyanate, p-tolylisocyanate, o-tolyl isocyanate, m-xylyl isocyanate, α-naphthyl isocyanate, octadecyl isocyanate, benzyl isocyanate, allyl isocyanate, cyclohexyl isocyanate, p-nitrophenyl isocyanate, o-chlorophenyl isocyanate, m-chlorophenyl isocyanate, p-fluorophenyl isocyanate, 4,4,4-trichloro-2-bromobutyl isocyanate, and the like, and polyisocyanates such as 2,4-tolylene diisocyanate, 2,6-tolylene diisocyanate, 4,4'-methylenebis(phenyl isocyanate), dianisidine diisocyanate, tolidine diisocyanate, hexamethylene diisocyanate, 4,4'-methylenebis(cyclohexyl isocyanate), m-xylene diisocyanate, 1,5-naphthalene diisocyanate, 1,4-diethylbenzene-β,β'-diisocyanate and other di- and higher polyisocyanates such as those listed in the tables of Siefken, supra. Mixtures of two or more of the above isocyanates can be used, such as mixtures of the 2,4- and 2,6-isomers of tolylene diisocyanate, mixtures of the 2,4'- and 4,4'-isomers of methylenebis(phenyl isocyanate) and the like. In addition to the 4,4'-methylenebis(phenyl isocyanate) or mixtures of the 2,4'-isomer and 4,4'-isomer thereof which are employed as the isocyanate component, there can also be used modified forms of these isocyanates. For example there can be used 4,4'-methylenebis(phenyl isocyanate), or an admixture thereof with a minor amount of the 2,4'-isomer, which has been treated to convert a minor proportion, generally less than 15% by weight of the starting material, to an artefact of said starting material. For example, the polyisocyanate component (I) can be methylenebis(phenyl isocyanate) which has been converted to a stable liquid at temperatures of about 15° C. and higher using, for example, the processes described in U.S. Pat. Nos. 3,384,653, 3,394,164 and 3,394,165.

In addition to the various modified forms of methylenebis(phenyl isocyanate) exemplified above there can also be employed as the polyisocyanate component a mixture of methylenebis(phenyl isocyanate) with polymethylene polyphenyl isocyanates of higher functionality. Such mixtures are generally those obtained by phosgenation of corresponding mixtures of methylene bridged polyphenyl polyamines. The latter, in turn, are obtained by interaction of formaldehyde, hydrochloric acid and primary aromatic amines, for example, aniline, o-chloroaniline, o-toluidine and the like. Such polyamines and polyisocyanates prepared therefrom are known in the art, see, for example, U.S. Pat. Nos. 2,683,730; 2,950,263; 3,012,008, and 3,097,191; Canadian Pat. No. 665,495; and German Pat. No. 1,131,877. Preferred polymethylene polyphenyl polyisocyanates are those containing from about 35% to about 60% by weight of methylenebis(phenyl isocyanate). The polymethylene polyphenyl isocyanate available commercially under the trademark PAPI ® is typical of this type of polyisocyanate.

The carboxylic acid intramolecular anhydrides which are employed in the process of the invention can be any mono- or poly intramolecular anhydride. Illustrative of the mono intramolecular anhydrides are phthalic anhydride, succinic anhydride, adipic anhydride, glutaric anhydride, citraconic anhydride, maleic anhydride, itaconic anhydride, fumaric anhydride, naphthalene-1,2-dicarboxylic acid anhydride, naphthalene-1,8-dicarboxylic acid anhydride, chlorendic anhydride, 1,2,3,6-tetrahydrophthalic acid anhydride, and the like. The polycarboxylic acids which are employed in the process of the invention contain at least two carboxylic moieties selected from the class consisting of free carboxy groups and anhydride groups. Said polycarboxylic derivatives are inclusive of aromatic, aliphatic, cycloaliphatic or heterocyclic polycarboxylic acids as well as the intramolecular and/or intermolecular anhydrides thereof, provided that, in the case of those anhydrides which contain a single anhydride group there is also present in the molecule at least one free carboxy group. As will be appreciated by one skilled in the art only those polycarboxylic acids which contain carboxy groups attached either to two adjacent carbon atoms or to two carbon atoms which are separated from each other by a single carbon or hetero-atom are capable of forming intra- as opposed to inter- molecular acid anhydrides.

Any of the aforesaid polycarboxylic acids or anhydrides can be employed as the polycarboxylic derivative in the process of the invention. As will be apparent to the skilled chemist the nature of the recurring units in the resulting polyimides will vary according to the structure of the starting polycarboxylic derivative.

When the polycarboxylic acid derivative is a dicarboxylic acid which is incapable of forming an intramolecular anhydride, the product formed in accordance with the process of the invention is a polyamide e.g. the product from said dicarboxylic acid and a diisocyanate would contain the recurring unit:

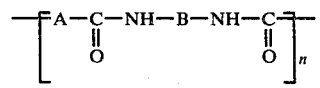

wherein A is the hydrocarbon residue of the dicarboxylic acid starting material and B is the hydrocarbon residue of the diisocyanate. On the other hand, when the polycarboxylic derivative is an intramolecular or inter-molecular anhydride which contains two or more anhydride moieties or contains one anhydride moiety and free carboxylic acid groups capable of intramolecular or inter-molecular anhydride formation, the product of reaction in accordance with the process of the invention is a polyimide e.g. the product of reaction of a diisocyanate and a polycarboxylic acid derivative containing two intra-molecular anhydride groups would contain the recurring unit:

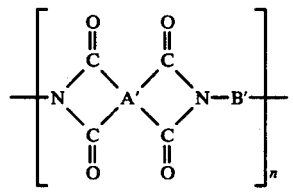

wherein A' is the hydrocarbon residue of the dianhydride and B' is the hydrocarbon residue of the diisocyanate.

Similarly where the polycarboxylic acid derivative contains one or more anhydride groups in addition to a free carboxylic acid group or groups, the polymer resulting from the process of the invention will be a hybrid containing both amide and imide linkages.

All of the above types of polymers can be prepared in accordance with the process hereinabove described and all fall within the scope of this invention. Thus, by appropriate choice of the polycarboxylic acid derivative it is possible to prepare any of a wide variety of polymers using the single step process of the invention.

Examples of polycarboxylic derivatives which can be employed as the free carboxylic acids or as intermolecular anhydrides formed from the same or different acids are: isophthalic acid, terephthalic acid, trimesic acid and phthalic acid. Examples of polycarboxylic derivatives which can be employed as the free carboxylic acids or intramolecular anhydrides thereof, are:

trimellitic acid and the anhydride thereof,
pyromellitic acid and the dianhydride thereof,
mellophanic acid and the anhydride thereof,
benzene-1,2,3,4-tetracarboxylic acid and the dianhydride thereof,
benzene-1,2,3-tricarboxylic acid and the anhydride thereof,
diphenyl-3,3',4,4'-tetracarboxylic acid and the dianhydride thereof,
diphenyl-2,2',3,3'-tetracarboxylic acid and the dianhydride thereof,
naphthalene-2,3,6,7-tetracarboxylic acid and the dianhydride thereof,
naphthalene-1,2,4,5-tetracarboxylic acid and the dianhydride thereof,
naphthalene-1,4,5,8-tetracarboxylic acid and the dianhydride thereof,
decahydronaphthalene-1,4,5,8-tetracarboxylic acid and the dianhydride thereof,
4,8-dimethyl-1,2,3,5,6,7-hexahydronaphthalene-1,2,5,6-tetracarboxylic acid and the dianhydride thereof,
2,6-dichloronaphthalene-1,4,5,8-tetracarboxylic acid and the dianhydride thereof,
2,7-dichloronaphthalene-1,4,5,8-tetracarboxylic acid and the dianhydride thereof,
2,3,6,7-tetrachloronaphthalene-1,4,5,8-tetracarboxylic acid and the dianhydride thereof,
phenanthrene-1,3,9,10-tetracarboxylic acid and the dianhydride thereof,
perylene-3,4,9,10-tetracarboxylic acid and the dianhydride thereof,
bis(2,3-dicarboxyphenyl)methane and the dianhydride thereof,
bis(3,4-dicarboxyphenyl)methane and the dianhydride thereof,
1,1-bis(2,3-dicarboxyphenyl)ethane and the dianhydride thereof,
1,1-bis(3,4-dicarboxyphenyl)ethane and the dianhydride thereof,
2,2-bis(2,3-dicarboxyphenyl)propane and the dianhydride thereof,
2,3-bis(3,4-dicarboxyphenyl)propane and the dianhydride thereof,
bis(3,4-dicarboxyphenyl)sulfone and the dianhydride thereof,
bis(3,4-dicarboxyphenyl)ether and the dianhydride thereof,
ethylene tetracarboxylic acid and the dianhydride thereof,
butane-1,2,3,4-tetracarboxylic acid and the dianhydride thereof,
cyclopentane-1,2,3,4-tetracarboxylic acid and the dianhydride thereof,
pyrrolidine-2,3,4,5-tetracarboxylic acid and the dianhydride thereof,
pyrazine-2,3,5,6-tetracarboxylic acid and the dianhydride thereof,
mellitic acid and the trianhydride thereof,
thiophen-2,3,4,5-tetracarboxylic acid and the dianhydride thereof, and
benzophenone-3,3', 4,4'-tetracarboxylic acid and the dianhydride thereof.

Other anhydrides which may be employed in the practice of the invention are; the intermolecular anhydride of trimellitic acid 1,2-anhydride (see, for example U.S. Pat. No. 3,155,687), the bisanhydrides disclosed in U.S. Pat. No. 3,277,117 [e.g. 4,4'-ethylene glycol bis-anhydro trimellitate and 4,4'-(2-acetyl-1,3-glycerol)bis-anhydro trimellitate] and the di-adducts of maleic acid or anhydride with styrene.

Illustrative of aliphatic dicarboxylic acids are glutaric, adipic, azelaic, pimelic, sebacic, decanedioic dodecanedioic, and brassylic acids.

The heterocyclic phosphorus compounds of formulae (I), (II) and (III) which are employed as catalysts in the process of the invention are known in the art, as are the methods for their preparation. Thus the compounds of formula (I) in which R is oxygen or sulfur are described in U.S. Pat. Nos. 2,663,737 and 2,663,738 and the corresponding compounds of formula (II) in which R is oxygen or sulfur are described in U.S. Pat. No. 2,663,739. The compounds of formulae (I) and (II) wherein R represents NR' (wherein R' is lower-hydrocarbyl) can be prepared from the corresponding compounds in which R represents oxygen by reacting the latter with the appropriate hydrocarbyl isocyanate R'NCO using the conditions described by G. Aksnes et al., J. Acta Chem. Scand. 23, 2697, 1969. The compounds of formula (III), which are employed in the process of the invention, and processes for their preparation, are described by S. E. Cremer et al., J. Org. Chem. 32, 4066 (1967).

The imides and amides produced in accordance with the process of the invention are, for the most part, known in the art and are useful in ways which are familiar to the art. For example, many of the monoimides, particularly those derived from chlorendic acid anhydride, are known to be useful as insecticides, fungicides, and herbicides. Illustratively, N-arylphthalimides such as N-phenylphthalimide, exhibit growth-regulatory effects and can be used for prevention of fruit drop, rooting of cuttings, formation of parthenogenic fruit, and the like; Canadian Pat. No. 519,684. N-arylphthalimides such as N-phenylphthalimide are also useful as stabilizers for polysulfone resins; U.S. Pat. No. 2,643,237.

The polyamides and polyamide-imides produced in accordance with the invention can be employed for a variety of purposes. Illustratively, they may be shaped, for example, by machining from billets, by punching or by making use of powdered metal techniques, into articles such as grinding wheels, friction devices such as brakes and clutches, or they may be used as coating compositions. Said coating compositions may be used as impregnating resins or applied to various substrates, such as metals, wires, woven fabrics or even to other polymeric materials.

The finding that the compounds of formulae (I), (II) and (III) will act as catalysts for the preparation of the imides, amides and amide-imides is highly surprising in view of the fact that the compounds in question are known to be highly active catalysts for the conversion of organic isocyanates to carbodiimides. Not only is the finding highly surprising, but it is also highly useful. In particular, it is found that, by employing the above compounds as catalysts, it is possible to produce polyamides and polyamide-imides which have higher molecular weights and more useful, i.e. superior, structural strength properties than those obtainable heretofore. Further, in contrast to the most successful catalysts hitherto employed in this art (such as sodium and potassium methoxide), the compounds (I), (II) and (III) are not basic and show no tendency to cause trimerization of the isocyanate as an undesirable side reaction.

In the case of the preparation of polyimides by condensation of an organic diisocyanate and a dianhydride it is found that the use of the heterocyclic compounds (I), (II) or (III) as catalysts gives rise to a polymer in which there are a substantial number of carbodiimide units in addition to the imide units. In the case of the preparation of polyamides and polyamide-imides no such formation of carbodiimide moieties occurs.

When the process of the invention is employed in the preparation of polymers, the process can be conducted so as to give either cellular or non-cellular products. The reaction between the isocyanate and the carboxylic acid or anhydride gives rise to elimination of carbon dioxide. The carbon dioxide can, if desired, be removed from the reaction mixture as it is produced and, in the absence of any other added blowing agent, the reaction will be non-cellular.

In preparing cellular products in accordance with the process of the invention, the polyisocyanate, the polycarboxylic acid or anhydride and the heterocyclic phosphorus catalyst (I), (II), or (III), are brought together under foam producing conditions using additional blowing agents, if desired, and like adjuvants commonly employed in the preparation of polymer foams of this type.

The following examples describe the manner and process of making and using the invention and set forth the best mode contemplated by the inventors of carrying out the invention but are not to be construed as limiting.

EXAMPLE 1

The reaction between phenyl isocyanate and benzoic acid was investigated without the use of a catalyst and then with a catalyst in accordance with the invention.

A mixture of 4.8 g. (0.04 mole) of phenyl isocyanate and 4.9 g. (0.04 mole) of benzoic acid in 50 ml. of anhydrous xylene was heated under reflux for 90 minutes. At the end of this period the infrared spectrum and an aliquot showed the complete absence of any amide linkage. Accordingly, a solution of 0.0658 g. (0.0005 mole) of a mixture of 1,3-dimethyl-2-phospholene-1-oxide and 1,3-dimethyl-3-phospholene-1-oxide in 1 ml. of anhydrous xylene was added to the reaction mixture, still at reflux, and the refluxing was continued for a further 35 minutes. The resulting product was allowed to cool to room temperature (circa 20° C.) and the solid which separated was isolated by filtration, washed with hexane and dried. There was thus obtained 7.1 g. (90 percent theoretical yield) of N-phenylbenzamide having a melting point of 157° to 159° C.

EXAMPLE 2

A mixture of 4.7 g (0.025 mole) of azelaic acid, 5.95 g. (0.05 mole) of phenyl isocyanate, and 0.0685 g. (0.0005 mole) of a mixture of 1,3-dimethyl-2-phospholene-1-oxide and 1,3-dimethyl-3-phospholene-1-oxide in 50 ml. of anhydrous xylene was heated under reflux for 10 minutes. At the end of this time the evolution of bubbles had subsided. The mixture was cooled to room temperature (circa 20° C.) and 50 ml. of benzene was added. The crystalline solid which separated was isolated by filtration, washed with hexane (2×50 ml.) and dried. There was thus obtained 7.4 g. (87.6 percent theoretical yield) of N,N'-diphenyl azelaic acid diamide having a melting point of 173°–181° C. Recrystallization from methanol raised the melting point to 185° to 186.5° C.

EXAMPLE 3

A mixture of 4.8 g. (0.025 mole) of trimellitic anhydride, 5.95 g. (0.05 mole) of phenyl isocyanate and 0.065 g. (0.0005 mole) of a mixture of 1,3-dimethyl-2-phospholene-1-oxide and 1,3-dimethyl-3-phospholene-1-oxide in 50 ml. of anhydrous xylene was heated under reflux for 3.5 hours. At the end of this time the mixture was cooled to room temperature (circa 20° C.) and diluted with 25 ml. of benzene. The solid which separated was isolated by filtration and washed with hexane (50 ml.). There was thus obtained 7.95 g. (93 percent theoretical yield) of N-phenyl-5-benzamidophthalimide in the form of a yellow solid having a melting point of 260° to 264° C.

EXAMPLE 4

A mixture of 7.4 g. (0.05 mole) of phthalic anhydride, 5.95 g. (0.05 mole) of phenyl isocyanate and 0.065 g. (0.0005 mole) of a mixture of 1,3-dimethyl-2-phospholene-1-oxide and 1,3-dimethyl-3-phospholene-1-oxide in 50 ml. of anhydrous xylene was heated under reflux for 3.5 hours. At the end of this time the mixture was cooled to room temperature (circa 20° C.) and the solid which separated was isolated by filtration, washed with hexane and dried. There was thus obtained 6.6 g. (59.1 percent theoretical yield) of N-phenylphthalimide in the form of a crystalline solid having a melting point of 191° to 203° C.

EXAMPLE 5

A mixture of 2.9 g. (0.025 mole) of maleic acid, 5.95 g. (0.05 mole) of phenyl isocyanate and 0.065 g. (0.005 mole) of a mixture of 1,3-dimethyl-2-phospholene-1-oxide and 1,3-dimethyl-3-phospholene-1-oxide in 50 ml. of anhydrous xylene was heated to reflux at which point the mixture became a solid mass. The product was diluted with 25 ml. of benzene and filtered. The solid was washed on the filter with 25 ml. of benzene followed by 50 ml. of hexane and then dried in vacuo. There was thus obtained 4.45 g. (66.9 percent theoretical yield) of N,N'-diphenyl maleic acid diamide in the form of a crystalline solid having a melting point of 303° to 309° C.

EXAMPLE 6

A mixture of 7.4 g. (0.05 mole) of phthalic anhydride and 5.95 g. (0.05 mole) of phenyl isocyanate and 0.097 g. (0.0005 mole) of 3-methyl-1-phenylphospholane-1-oxide in 50 ml. of anhydrous xylene was heated under reflux for 3.5 hours. At the end of this time the mixture was cooled to room temperature and the solid which separated was isolated by filtration, washed with 50 ml. of xylene followed by 2×25 ml. of hexane and dried. There was thus obtained 3.9 g. (34.9 percent theoretical yield) of N-phenylphthalimide having a melting point of 204°-8° C.

EXAMPLE 7

A mixture of 7.4 g. (0.05 mole) of phthalic anhydride, 4.96 g. (0.05 mole) of n-butyl isocyanate and 0.0532 g. (0.0004 mole) of a mixture of 1,3-dimethyl-2-phospholene-1-oxide and 1,3-dimethyl-3-phospholene-1-oxide in 50 ml. of xylene was heated under reflux for 3.75 hours. The resulting mixture was distilled to remove the xylene and the residue was distilled under vacuum to obtain a total of 9.8 g. of semi-solid material having a boiling point of 142°-170° C./0.3 mm. An aliquot of 2 g. of this material was triturated with 50 ml. of hexane. The insoluble phthalic anhydride (0.15 g.) was removed by filtration and the filtrate was evaporated to dryness to yield 1.95 g. of N-n-butylphthalimide having a melting point of 32°-35.5° C. On the basis of the yield from this aliquot, it is calculated that the total amount of N-n-butylphthalimide in the crude product was 9 g. representing an 87% theoretical yield.

EXAMPLE 8

A mixture of 18.82 g. (0.1 mole) of azelaic acid, 19.21 g. (0.1 mole) of trimellitic anhydride and 0.07 g. (0.00053 mole) of 1,3-dimethyl-3-phospholene-1-oxide was charged to a dry 500 ml. round bottom flask fitted with gas inlet tube, stirrer, condenser and addition funnel. To the mixture was added 298 ml. of tetramethylene sulfone which had been previously distilled under vacuum. The resulting mixture was stirred under an atmosphere of nitrogen and heated to 150° C. at which point the mixture was a clear pale yellow solution. The temperature was maintained at 150° C. while a total of 50.05 g. (0.2 mole) of 4,4'-methylenebis(phenyl isocyanate) in 60 ml. of tetramethylenesulfone was added dropwise over a period of 6 hours and 40 minutes. The mixture was then cooled to room temperature (circa 20° C.) and poured, with stirring, into an excess of acetone. The solid which separated was isolated by filtration and then washed by suspending the product in water with vigorous stirring, isolating the washed product by filtration, resuspending the solid in acetone with vigorous stirring, and finally isolating by filtration followed by drying. There was thus obtained 70 g. of a polyamide-imide in which 50 percent of the recurring units had the formula

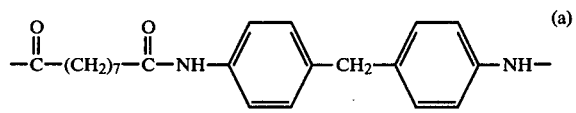

and the remaining 50 percent of the recurring units had the formula

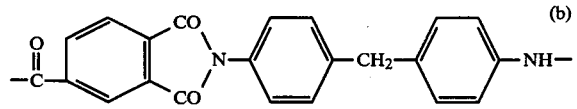

A sample of the polyamide-imide was dried at 170° C. for 12 hours. The inherent viscosity of this sample (0.5 percent in N-methylpyrrolidone at 30° C.) was found to be 1.25.

The above procedure was repeated and a sample of the powdered polymer so obtained was blended with 2 percent by weight of an antioxidant (Irganox 1098) and extruded through a ⅛ inch diameter die using a Brabender extruder. The barrel temperature in Zones 1 and 2 of the latter was 270° C., in Zone 3 265° C. and the temperature of the die was 260° C. The screw speed was 50 rpm with a 4:1 compression ratio. The extruded strands were pelletized using a cutter and the pelletized material was then injection molded using an Arburg reciprocating screw injection molding machine to produce test bars for examination of tensile and flexural strength properties under the following conditions.

|  | Tensile Bars | Flexural Bars |
| --- | --- | --- |
| Temperature °C. |  |  |
| Barrel - Zone 1 | 270 | 270 |
| Zone 2 | 270 | 270 |
| nozzle | 270 | 270 |
| mold | 160 | 150 |
| Injection pressure: psi | 8700 | 10200 |
| Injection speed setting | 4.2 | 4.2 |
| Screw speed | 120 | 120 |
| Back pressure: psi | 0 | 0 |
| Injection time: seconds | 12 | 12 |
| Mold close: seconds | 35 | 35 |

The following physical properties of the polymer were determined using the test bars so prepared:

| Tensile Strength | (yield) | psi | 14,050 |
| --- | --- | --- | --- |
|  | (break) | psi | 12,500 |
| Tensile Modulus |  | psi | 330,000 |
| Elongation | (break) | % | 16.5 |
|  | (yield) | % | 8.4 |
| Flexural Strength |  | psi | 17,240 |
| Flexural Modulus |  | psi | 323,600 |
| IZOD Impact Strength | Unnotched ft. lbs/in |  | >20 |
|  | Notched ft. lbs/in |  | 3.04 |
|  |  |  | ¼" thick bar |
| Heat distortion temperature at 264 psi |  | °C. | 150 |

EXAMPLE 9

The procedure described in Example 8 was repeated except that the amount of azelaic acid was increased to 22.58 g. (0.12 mole), the amount of trimellitic anhydride was decreased by a corresponding amount to 15.37 g. (0.08 mole), the amount of 1,3-dimethyl-3-phospholene-1-oxide was increased to 0.10 g. (0.00076 mole) and the amount of tetramethylenesulfone was reduced to 164 ml. to give a mixture with 20 percent by weight of solids. In spite of the increased concentration of solids so achieved, the final reaction mixture was still sufficiently low in viscosity to be handled by standard stirring equipment. The resulting polyamide-imide was worked up as described in Example 8 and a sample was dried under vacuum at 88° C. The dried sample showed inherent viscosity (0.5 percent in m-cresol) at 30° C. of 1.12. Said polyamide-imide had 60 percent of recurring units of formula (a) [see Example 8] and 40 percent of formula (b).

EXAMPLE 10

A mixture of 30.74 g. (0.16 mole) of trimellitic anhydride, 6.65 g. (0.04 mole) of isophthalic anhydride and 0.08 g. (0.0006 mole) of 1,3-dimethyl-3-phospholene-1-oxide was charged to a dry 500 ml. round bottom flask fitted with gas inlet tube, stirrer, condenser and addition funnel. To the mixture was added 192 ml. of tetramethylenesulfone which had been previously redistilled. The resulting mixture was stirred under nitrogen and heated to 160° C. The mixture was maintained at the same temperature with stirring while a total of 50.05 g. (0.20 mole) of 4,4'-methylenebis(phenyl isocyanate) in 60 ml. of tetramethylenesulfone was added dropwise over a period of 5.75 hours. After the addition was complete, the mixture was stirred for a further 10 minutes before being poured hot into circa 3 liters of deionized water. The spaghetti-like mass which was precipitated, was allowed to stand overnight before being chopped up and washed by suspending in deionized water with vigorous stirring. The washed solid was isolated by filtration and the washing step was repeated twice with water and once with acetone and, finally, the solid was stirred in an acetone suspension overnight. The resulting solid was isolated by filtration and dried at 210° C. for 17 hours. A sample of the dried solid was found to have an inherent viscosity (0.5 percent in N-methylpyrrolidone) at 30° C. of 0.551. Three molded discs (2"×⅛") were prepared by compression molding at 295°–302° C. under a pressure of 4450 psi. A Gehman test (ASTM-D1053-58T) was run on a speciment of the molded material and showed a glass transition temperature (Tg) of 263° C.

The above preparation was repeated exactly as described except that the quantities of all reactants were increased by 50 percent and the total amount of tetramethylenesulfone was increased to 475 ml. to yield a reaction product having 15 percent w/w solids. The polymer so obtained was found to have an inherent viscosity (0.5 percent in N-methyl-pyrrolidone at 30° C.) of 1.28.

A solution of 15 g. of said polymer in 135 ml. of dimethylformamide was filtered and the filtrate was used to cast 3 films employing a Gardner film casting apparatus with a knife setting of 25 mils. The films so obtained were predried over glass plates at 80° C. for circa 3 hours before being removed and clamped on frames for a final cure at 200° C. for 10 hours. The following properties were determined using specimens of the film so obtained.

|  | parallel to casting direction | perpendicular to casting direction |
|---|---|---|
| Tensile strength: psi | 13,800 | 14,600 |
| Tensile modulus: psi | 342,500 | 331,600 |
| Elongation at break: % | 25.0 | 20.0 |

EXAMPLE 11

A mixture of 19.05 g. (0.1 mole) of azelaic acid, 19.21 g. (0.1 mole) of trimellitic anhydride and 0.08 g. (0.0004 mole) of 3-methyl-1-phenyl-2-phospholene-1-oxide was charged to a dry 500 ml. round bottom flask fitted with gas inlet tube, stirrer, condenser, and addition funnel. To the mixture was added 214 ml. of redistilled tetramethylenesulfone and the resulting mixture was heated under nitrogen to 150° C. with stirring. The mixture was maintained at that temperature while a total of 50.05 g. (0.2 mole) of 4,4'-methylenebis(phenyl isocyanate) in 60 ml. of tetramethylenesulfone was added dropwise with stirring over a period of 6.5 hours. When the addition was complete, the reaction mixture was maintained at the above temperature with stirring before being poured, while still hot, into an excess of deionized water. The resulting mixture was allowed to stand for 3 days after which the solid which had precipitated was chopped up, washed by suspending in water with vigorous stirring, filtered, washed again with water and then with acetone, and finally suspended overnight in acetone before filtering and drying under vacuum at 173° C. for 40 hours. The material so obtained was a copolyamide-imide characterized by the presence of equal numbers of recurring units (a) and (b) [see Example 8]. The polyamide-imide had an inherent viscosity (0.5 percent in N-methylpyrrolidone) of 1.10. A disc (2"×⅛") was compression molded at 260° C. under a pressure of 4450 psi and found to have the following physical properties: A Gehman test was run according to ASTM D1053-58T and showed a Tg of 170° C.

EXAMPLE 12

A mixture of 15.03 g. (0.09 mole) of isophthalic acid and 125 ml. of tetramethylenesulfone was charged to a 300 ml. round bottom flask fitted with stirrer, gas inlet tube, condenser and addition funnel. The mixture was heated to 160° C. under nitrogen with stirring and 0.07 g. (0.00054 mole) of 1,3-dimethyl-3-phospholene-1-oxide was added. The mixture was stirred and maintained at circa 160° C. while a solution 5.23 g. (0.03 mole) of 2,4-toluene diisocyanate in 10 ml. of tetramethylenesulfone was added dropwise over a period of 45 minutes. After the addition was completed, the mixture was stirred at the same temperature for 2 hours at the end of which time the product was a clear solution. To this solution was added 11.40 g. (0.06 mole) of azelaic acid which was rinsed in with 40 ml. of tetramethylenesulfone. This addition was followed by the dropwise addition, with stirring and maintenance of the temperature at the above level, of a solution of 30.04 g. (0.12 mole) of 4,4'-methylenebis(phenyl isocyanate) in 25 ml. of tetramethylenesulfone. The addition was completed in 4 hours and the residual isocyanate in the addition funnel was rinsed in using 20 ml. of tetramethylenesulfone. After the addition was complete, the reaction mixture was stirred for a further 1 hour at 160° C. before being poured hot into 3 l. of cold water. The solid which separated was allowed to stand overnight before being chopped, isolated by filtration and resuspended in water. The solid so washed was isolated by filtration, then suspended in acetone. The suspension was stirred overnight and then filtered, washed by suspension in acetone and then filtered and dried for 2 hours at 80° C., followed by 1 hour at 110° C. and 12 hours at 160° C., all under vacuum. A sample of the material was found to have an inherent viscosity (0.5 percent in m-cresol) of 0.73 at 30° C.

For purposes of comparison a second run was carried out exactly as described above except that the 1,3-dimethyl-3-phospholene-1-oxide catalyst was replaced by 0.07 g. sodium methoxide. The resulting polyamide had an inherent viscosity (0.5 percent in m-cresol) at 30° C. of only 0.34 indicating a markedly lower average molecular weight for this polymer as compared with that prepared in accordance with the process of the invention under identical conditions.

We claim:

1. In a process for catalyzing the amide and or imide-forming reaction between substantially stoichiometric proportions of an organic isocyanate and a member selected from the class consisting of organic carboxylic acids and organic carboxylic anhydrides, the improvement which comprises employing as the catalyst from 0.0001 mole to 0.1 mole, per mole of isocyanate, of a cyclic phosphorus compound selected from those having the formulae:

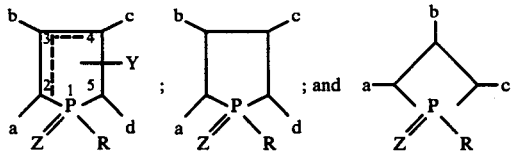

wherein a, b, c and d in each instance are selected from the group consisting of hydrogen, halogen, lower-alkoxy, phenoxy, lower-hydrocarbyl and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of hydrocarbyl and halo-substituted hydrocarbyl, the hydrocarbyl in each instance having from 1 to 12 carbon atoms, inclusive; and Z is selected from the class consisting of oxygen, sulfur and NR' wherein R' is hydrocarbyl from 1 to 12 carbon atoms, inclusive.

2. In a process for the preparation of a polyimide by condensation of an organic diisocyanate with substantially stoichiometric proportion of a member selected from the class consisting of organic tetracarboxylic acids capable of forming intramolecular dianhydrides and the corresponding intramolecular dianhydrides thereof, the improvement which comprises employing as the catalyst from 0.0001 mole to 0.1 mole, per mole of isocyanate, of a cyclic phosphorus compound selected from those having the formulae:

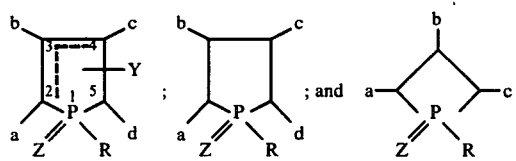

wherein a, b, c and d in each instance are selected from the group consisting of hydrogen, halogen, lower-alkoxy, phenoxy, lower-hydrocarbyl and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of hydrocarbyl and halo-substituted hydrocarbyl, the hydrocarbyl in each instance having from 1 to 12 carbon atoms, inclusive; and Z is selected from the class consisting of oxygen, sulfur and NR' wherein R' is hydrocarbyl from 1 to 12 carbon atoms, inclusive.

3. The process of claim 2 wherein the cyclic phosphorus compound is a mixture of 1,3-dimethyl-3-phospholene-1-oxide and 1,3-dimethyl-2-phospholene-1-oxide.

4. The process of claim 3 wherein the cyclic phosphorus compound is 1-phenyl-3-methyl-3-phospholene-1-oxide.

5. The process of claim 3 wherein the cyclic phosphorus compound is 3-methyl-1-phenylphospholane-1-oxide.

6. In a process for the preparation of a polyamide by condensation of substantially stoichiometric proportions of an organic diisocyanate and an organic dicarboxylic acid, the improvement which comprises employing as the catalyst from 0.0001 mole to 0.1 mole, per mol of isocyanate, of a cyclic phosphorus compound selected from those having the formulae:

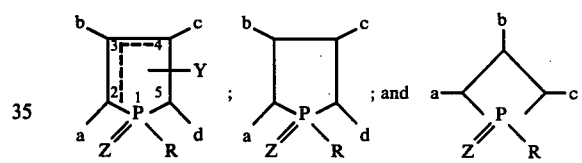

wherein a, b, c and d in each instance are selected from the group consisting of hydrogen, halogen, lower-alkoxy, phenoxy, lower-hydrocarbyl and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of hydrocarbyl and halo-substituted hydrocarbyl, the hydrocarbyl in each instance having from 1 to 12 carbon atoms, inclusive; and Z is selected from the class consisting of oxygen, sulfur and NR' wherein R' is hydrocarbyl from 1 to 12 carbon atoms, inclusive.

7. The process of claim 6 wherein the cyclic phosphorus compound is a mixture of 1,3-dimethyl-2-phospholene-1-oxide and 1,3-dimethyl-3-phospholene-1-oxide.

8. The process of claim 6 wherein the cyclic phosphorus compound is 1-phenyl-3-methyl-2-phospholene-1-oxide.

9. The process of claim 6 wherein the cyclic phosphorus compound is 3-methyl-1-phenylphospholane-1-oxide.

10. In a process for the preparation of a polyamide-imide by condensation of substantially stoichiometric proportions of an organic diisocyanate and an organic dicarboxylic acid anhydride which also contains a free carboxylic acid group, the improvement which comprises employing as the catalyst from 0.0001 mole to 0.1 mole, per mole of isocyanate, of a cyclic phosphorus compound selected from those having the formulae:

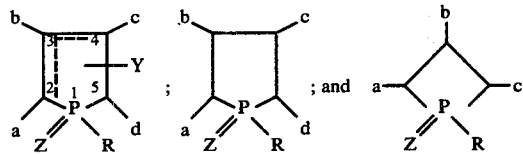

wherein a, b, c and d in each instance are selected from the group consisting of hydrogen, halogen, lower-alkoxy, phenoxy, lower-hydrocarbyl and halo-substituted lower-hydrocarbyl; the dotted lines represent a double bond between carbon atom 3 and one of the carbon atoms 2 and 4; Y is hydrogen attached to whichever of carbon atoms 2 and 4 is not part of said double bond; R is selected from the group consisting of hydrocarbyl and halo-substituted hydrocarbyl, the hydrocarbyl in each instance having from 1 to 12 carbon atoms, inclusive; and Z is selected from the class consisting of oxygen, sulur and NR' wherein R' is hydrocarbyl from 1 to 12 carbon atoms, inclusive.

11. The process of claim 10 wherein the cyclic phosphorus compound is a mixture of 1,3-dimethyl-2-phospholene-1-oxide and 1,3-dimethyl-3-phospholene-1-oxide.

12. The process of claim 10 wherein the cyclic phosphorus compound is 1-phenyl-3-methyl-2-phospholene-1-oxide.

13. The process of claim 10 wherein the cyclic phosphorus compound is 3-methyl-1-phenylphospholane-1-oxide.

14. In a process for the preparation of a polyimide by condensing equimolar proportions of benzophenone-3,3',4,4'-tetracarboxylic dianhydride and a mixture of 4,4'-methylenebis(phenyl isocyanate) and toluene diisocyanate, the improvement which comprises carrying out said reaction in the presence of a catalytic amount of a mixture of 1,3-dimethyl-2-phospholene-1-oxide and 1,3-dimethyl-3-phospholene-1-oxide.